United States Patent [19]

Van Dyke et al.

[11] Patent Number: 4,606,751

[45] Date of Patent: Aug. 19, 1986

[54] BIOLOGICAL METHOD OF CONTROLLING JOHNSON GRASS AND SIMILAR WEEDS IN AGRICULTURAL CROPS

[75] Inventors: Cecil G. Van Dyke; Richard S. Winder, both of Raleigh, N.C.

[73] Assignee: North Carolina State University, Raleigh, N.C.

[21] Appl. No.: 679,260

[22] Filed: Dec. 7, 1984

[51] Int. Cl.4 .............................................. A01N 63/04
[52] U.S. Cl. ....................................... 71/79; 435/911; 47/DIG. 11
[58] Field of Search ............................ 71/79; 435/911; 47/DIG. 11

[56] References Cited

U.S. PATENT DOCUMENTS

| | | | |
|---|---|---|---|
| 3,357,895 | 12/1967 | Cherry | 71/79 |
| 3,849,104 | 11/1974 | Daniel et al. | 71/79 |
| 3,999,973 | 12/1976 | Templeton | 71/79 |
| 4,390,360 | 6/1983 | Walker | 71/79 |
| 4,419,120 | 12/1983 | Walker | 71/79 |

OTHER PUBLICATIONS

Myers et al., "Hydrogen Cyanide Potential, etc.," (1978) CA 89: 126273x (1978).

Gardner et al, "Handbook of Chemical Synonyms, etc.," CRC Press, Boca Raton, Florida (1983).

*Primary Examiner*—Glennon H. Hollrah
*Assistant Examiner*—Andrew Duff Meikle
*Attorney, Agent, or Firm*—Bell, Seltzer, Park & Gibson

[57] ABSTRACT

A biological method of controlling johnson grass and similar weeds in agricultural crops is provided in which *Bipolaris sorghicola* spores are suspended in a solution of water and a surfactant and sprayed onto a field in which the johnson grass or similar weed is growing in an amount sufficient to coat the leaves of the plants to be controlled. The *Bipolaris sorghicola* will kill the johnson grass and similar weeds without adversely affecting most agricultural crops.

6 Claims, No Drawings

BIOLOGICAL METHOD OF CONTROLLING JOHNSON GRASS AND SIMILAR WEEDS IN AGRICULTURAL CROPS

FIELD OF THE INVENTION

The present invention relates to the use of a mycoherbicide for controlling johnson grass.

BACKGROUND OF THE INVENTION

The effective control of weeds in fields in which agricultural crops are grown has been a continuing problem since farming began. Weed control measures have varied from cultivation to chemical herbicides. While providing weed control to varying degrees, each of the heretofore employed weed control measures have presented problems, disadvantages and deficiencies. For example, cultivation is time-consuming, expensive and results in soil erosion. Chemical herbicides present ecological problems by introducing toxic and sometimes non-biodegradable substances into the ecosystem.

Johnson grass (*Sorghum halepense*) is a weed that is sometimes difficult to control in agricultural crops because it is extremely hardy and propagates from both seeds and rizomes. Cultivation is therefore not very effective in the control of johnson grass. While certain chemical herbicides provide some measure of control, particularly in the seedling stage, these chemicals present problems from an ecological standpoint, as discussed above.

With the foregoing in mind, it is an object of the present invention to provide a biological method of controlling johnson grass and similar weeds in agricultural crops which is effective and which does not present ecological problems.

DESCRIPTION OF THE INVENTION

We have discovered in greenhouse tests that *Bipolaris sorghicola* can be used as a mycoherbicide for controlling johnson grass and it is believed that it may be effective when formulated for similar use in agricultural crops. Since this organism is part of the natural ecosystem (i.e. it is readily isolated from johnson grass), it does not present ecological problems like chemical herbicides.

The method of the present invention includes the provision of sufficient spores of *Bipolaris sorghicola* to produce a sufficient amount of the mycoherbicide for application. The initial spores may be obtained by isolating the fungus from diseased johnson grass plants obtained in the field or from previously grown spores. Other names for the fungus *Bipolaris sorghicola* include *Helminthosporium sorghicola* and *Drechslera sorghicola*.

In our tests, spores were grown in a growth medium consisting of CZ8 medium (a mixture of equal parts of corn leaf extract and vegetable juice) and agar, which was then formed into solid plates. Seed spores are applied to the center of each plate and permitted to grow until the plate is substantially covered (about 5–10 days). Any suitable growth medium may be used and the foregoing is merely one example of such a suitable medium.

The spores are then harvested from the plates and a mycoherbicide is prepared by suspending the spores in water to which a surfactant has been added. Preferably, the solution of water and surfactant has a surfactant concentration of about 0.03%. The surfactant we used was sold under the trademark "TERGITOL" by the Union Carbide Company. The mycoherbicide should preferably have a spore concentration of at least about $1.5 \times 10^5$ spores per ml of solution.

The mycoherbicide is then applied to the johnson grass to be controlled by spraying the spore containing solution onto the johnson grass in an amount sufficient to coat the leaves of the johnson grass. One application will usually be sufficient, but repeat applications may be made if necessary. Also, the method of the present invention may be used in addition to or in conjunction with other control measures.

EXPERIMENT I

A mycoherbicide having a spore concentration of $1.5 \times 10^5$ spores/ml was prepared as described above and sprayed onto approximately 5 day old johnson grass seedlings until run off. Out of 110 seedlings sprayed, 66% were dead after 6 days and there was heavy damage to the remainder.

EXPERIMENT II

A mycoherbicide having a spore concentration of $2.0 \times 10^7$ spores/ml was prepared as described above and sprayed onto approximately 5 day old johnson grass seedlings in an amount sufficient to coat the leaves but less than to run off. Out of 80 seedlings sprayed, 71 were dead after 8 days and the remaining 9 were dying. All plants were dead after 25 days from application of the mycoherbicide.

At the same time, the mycoherbicide was tested on certain crop plants and other weeds, including pumpkin, zinnia, wheat, peanut, soybean, okra, tomato, carrot, pearl millet, giant foxtail, foxtail millet, switch grass, broad leaf signal grass, yellow foxtail, tobacco, morning glory and corn. No symptoms were observed on any of these plants except pearl millet and switch grass and a slight hypersensitive reaction on corn.

It is believed that in addition to johnson grass the method of the present invention will be effective in controlling other related weeds. The use of the method of this invention to control these other weeds and any others against which *Bipolaris sorghicola* is effective is within the scope of the present invention.

In the specification there has been set forth the best mode presently contemplated for the practice of the present invention, and although specific terms are employed, they are used in a generic and descriptive sense only and not for purposes of limitation, the scope of the invention being defined in the claims.

That which is claimed is:

1. A method for selectively controlling johnson grass in an agricultural field containing crop plants and postemergent johnson grass, said method comprising inoculating said agricultural field with an effective amount of the fungus *Bipolaris sorghicola* which is selectively toxic to said johnson grass without causing substantial harm to said crop plants.

2. The method of claim 1, wherein the fungus *Bipolaris sorghicola* is applied to the agricultural field as a spray.

3. The method of claim 1, wherein the fungus *Bipolaris sorghicola* is applied to the agricultural field as an aqueous solution.

4. The method of claim 1, wherein the fungus *Bipolaris sorghicola* is applied to the agricultural field as a spore containing solution having a spore concentration of from about 1.5×10⁵ spores per milliliter to about 2.0×10⁷ spores per milliliter of solution.

5. The method of claim 1, wherein said crop plants are selected from the group of plants consisting of pumpkin, zinnia, wheat, peanut, soybean, okra, tomato, carrot, pearl millet, tobacco and corn.

6. A method for selectively controlling johnson grass in an agricultural field containing crop plants and postemergent johnson grass, said method comprising spraying said agricultural field with an aqueous solution of the fungus *Bipolaris sorghicola*, said fungus being selectively toxic to said johnson grass without causing substantial harm to said crop plants, said solution having a concentration of at least about 1.5×10⁵ spores per milliliter, to control said johnson grass without causing substantial harm to said crop plants.

* * * * *